US010806878B2

(12) United States Patent
Winski et al.

(10) Patent No.: US 10,806,878 B2
(45) Date of Patent: Oct. 20, 2020

(54) SYSTEM AND METHOD FOR DETERMINING A TARGET SUBJECT INTERFACE TEMPERATURE BASED ON A BASELINE TEMPERATURE

(71) Applicant: KONINKLIJKE PHILIPS N.V., Eindhoven (NL)

(72) Inventors: Jeffrey Ronald Winski, Irwin, PA (US); Richard Charles Dombrowski, Jr., Trafford, PA (US); David John Myers, Trafford, PA (US); Michael Joseph Mussallem, Pittsburgh, PA (US); Kevin Michael Bowen, Pittsburgh, PA (US); Brian John Bunofsky, Cranberry Township, PA (US); Benjamin Alfred Giovannelli, Gibsonia, PA (US); Jason Hauris Daschbach, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1166 days.

(21) Appl. No.: 14/378,348

(22) PCT Filed: Feb. 7, 2013

(86) PCT No.: PCT/IB2013/051002
§ 371 (c)(1),
(2) Date: Aug. 13, 2014

(87) PCT Pub. No.: WO2013/124755
PCT Pub. Date: Aug. 29, 2013

(65) Prior Publication Data
US 2015/0007821 A1    Jan. 8, 2015

Related U.S. Application Data

(60) Provisional application No. 61/601,595, filed on Feb. 22, 2012.

(51) Int. Cl.
*A61M 16/00* (2006.01)
*A61M 16/10* (2006.01)
(Continued)

(52) U.S. Cl.
CPC .... *A61M 16/0051* (2013.01); *A61M 16/0003* (2014.02); *A61M 16/0057* (2013.01);
(Continued)

(58) Field of Classification Search
CPC .......... A61M 16/0051; A61M 16/0003; A61M 16/0057; A61M 16/06; A61M 16/1075;
(Continued)

(56) References Cited

U.S. PATENT DOCUMENTS 5,915,379 A * 6/1999 Wallace ............ A61M 16/0051
                                                              128/204.18
6,105,575 A    8/2000 Estes et al.
(Continued)

FOREIGN PATENT DOCUMENTS

WO    2006126900 A1    11/2006
WO    2008091164 A1    7/2008
WO    2011151739 A1    12/2011

*Primary Examiner* — Timothy A Stanis
*Assistant Examiner* — Victoria Murphy (57) ABSTRACT

The present disclosure pertains to a pressure support system configured to provide pressure support therapy to a subject, wherein the pressure support system comprises a subject interface heater configured to controllably heat a pressurized flow of breathable gas to a target temperature that is offset from a baseline temperature. The breathable gas baseline temperature target offset ensures the gas delivered to the subject is delivered at a comfortable temperature and/or humidity level that does not cause airway dryness or result in condensed water in the subject interface. In one embodiment, the pressure support system comprises one or more of a pressure generator, a subject interface, a subject interface heater, one or more subject interface temperature sensors,
(Continued)

one or more baseline temperature sensors, one or more general sensors, a humidifier, a user interface, a processor, electronic storage, and/or other components.

18 Claims, 2 Drawing Sheets

(51) Int. Cl.
*A61M 16/16* (2006.01)
*A61M 16/06* (2006.01)

(52) U.S. Cl.
CPC .......... *A61M 16/024* (2017.08); *A61M 16/06* (2013.01); *A61M 16/1075* (2013.01); *A61M 16/16* (2013.01); *A61M 16/0069* (2014.02); *A61M 16/109* (2014.02); *A61M 16/1085* (2014.02); *A61M 16/1095* (2014.02); *A61M 16/161* (2014.02); *A61M 2016/003* (2013.01); *A61M 2016/0027* (2013.01); *A61M 2205/3368* (2013.01); *A61M 2205/3653* (2013.01); *A61M 2205/50* (2013.01); *A61M 2205/502* (2013.01); *A61M 2230/005* (2013.01); *A61M 2230/50* (2013.01)

(58) Field of Classification Search
CPC ............... A61M 16/16; A61M 16/161; A61M 2205/50; A61M 2230/005; A61M 2230/50; A61M 16/1095; A61M 16/1085; A61M 16/0069; A61M 2205/3653; A61M 2205/3368; A61M 2016/003; A61M 2205/3372; A61M 16/109
See application file for complete search history.

(56) References Cited

U.S. PATENT DOCUMENTS

| | | | | |
|---|---|---|---|---|
| 6,142,146 | A * | 11/2000 | Abrams | A61M 15/0085 128/203.15 |
| 2004/0221844 | A1 | 11/2004 | Hunt et al. | |
| 2007/0169776 | A1 | 7/2007 | Kepler et al. | |
| 2009/0110379 | A1* | 4/2009 | McGhin | A61M 16/1075 392/485 |
| 2010/0132707 | A1 | 6/2010 | Muller | |
| 2010/0186743 | A1* | 7/2010 | Kane | A61M 16/0003 128/204.23 |
| 2010/0269824 | A1* | 10/2010 | Friberg | A61M 16/021 128/203.13 |
| 2012/0037156 | A9 | 2/2012 | Stanislav et al. | |

* cited by examiner

SYSTEM AND METHOD FOR DETERMINING A TARGET SUBJECT INTERFACE TEMPERATURE BASED ON A BASELINE TEMPERATURE

CROSS-REFERENCE TO PRIOR APPLICATIONS

This application is the U.S. National Phase application under 35 U.S.C. § 371 of International Application Serial No. PCT/IB2013/051002, filed on Feb. 7, 2013, which claims the benefit of U.S. Application Ser. No. 61/601,595, filed on Feb. 22, 2012. These applications are hereby incorporated by reference herein.

BACKGROUND

1. Field

The present disclosure pertains to a pressure support system configured to provide pressure support therapy to a subject, wherein the pressure support system comprises a subject interface heater configured to controllably heat a pressurized flow of breathable gas to a target temperature that is offset from a baseline temperature.

2. Description of the Related Art

It is well known to treat sleep disordered breathing by applying a positive air pressure (PAP) to the patient's airway. This positive pressure effectively "splints" the airway, thereby maintaining an open passage to the lungs. In one type of PAP therapy, known as continuous positive air pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

Humidifiers are frequently provided between or integral with a PAP machine and the user interface in order to humidify the otherwise relatively dry compressed air generated by the PAP machine. Within the humidifier, water is allowed to evaporate to produce vapor within a reservoir while breathing gas is passed over the surface of the water. Increased water vapor within the reservoir increases the capability to provide more humidity to the gas that is delivered to a user. In a heated passover type of humidifier, this increase in gas stream humidity is accompanied by an increase in the gas stream temperature. When the ambient temperature around the PAP machine is below the gas stream temperature, condensation can form on the inside of the patient breathing circuit.

It is presently known to heat the patient breathing circuit in order to reduce the formation of condensation on and/or within the patient breathing circuit. In current systems, the patient circuit is heated by providing a constant amount of heat to the patient circuit in an effort to maintain a constant temperature.

SUMMARY

Accordingly, one or more aspects of the present disclosure relate to a pressure support system configured to provide temperature controlled pressure support to a subject. In some embodiments, the pressure support system comprises a pressure generator, a subject interface, a subject interface heater, one or more baseline temperature sensors, and one or more processors. In some embodiments, the one or more processors comprise a baseline temperature module, an offset temperature module, a target temperature module, and/or a subject interface heater control module. The pressure generator is configured to generate a pressurized flow of breathable gas for delivery to an airway of the subject. The subject interface is configured to deliver the pressurized flow of breathable gas to the airway of the subject. The subject interface heater is configured to controllably heat the pressurized flow of breathable gas in the subject interface. The one or more baseline temperature sensors are configured to generate one or more output signals conveying information related to a baseline temperature. The baseline temperature module is configured to determine the baseline temperature based on the output signals generated by the baseline temperature sensors. The offset temperature module is configured to obtain a temperature offset. The target temperature module is configured to determine a target temperature based on the baseline temperature and the temperature offset. The subject interface heater control module is configured to control the subject interface heater to maintain the temperature of the pressurized flow of breathable gas at the target temperature.

Yet another aspect of the present disclosure relates to a method of providing temperature controlled pressure support to a subject. The method comprises generating a pressurized flow of breathable gas for delivery to an airway of the subject; delivering the pressurized flow of breathable gas to the airway of the subject; controllably heating the pressurized flow of breathable gas; generating one or more output signals conveying information related to a baseline temperature; determining the baseline temperature based on the output signals conveying information related to a baseline temperature; obtaining a temperature offset; determining a target temperature based on the baseline temperature and the temperature offset; and controlling the temperature of the pressurized flow of breathable gas at the target temperature.

Still another aspect of the present disclosure relates to a pressure support system configured to provide temperature controlled pressure support to a subject. In some embodiments, the pressure support system comprises means to generate a pressurized flow of breathable gas for delivery to an airway of the subject; means to deliver the pressurized flow of breathable gas to the airway of the subject; means to controllably heat the pressurized flow of breathable gas in the means to communicate with the airway of the subject; means to generate one or more output signals conveying information related to a baseline temperature; and means to execute computer program modules. In some embodiments, the computer program modules comprise means to determine the baseline temperature based on the output signals generated by the means to generate one or more output signals conveying information related to a baseline temperature; means to obtain a temperature offset; means to determine a target temperature based on the baseline temperature and the temperature offset; and means to control the means to controllably heat to maintain the temperature of the pressurized flow of breathable gas at the target temperature.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
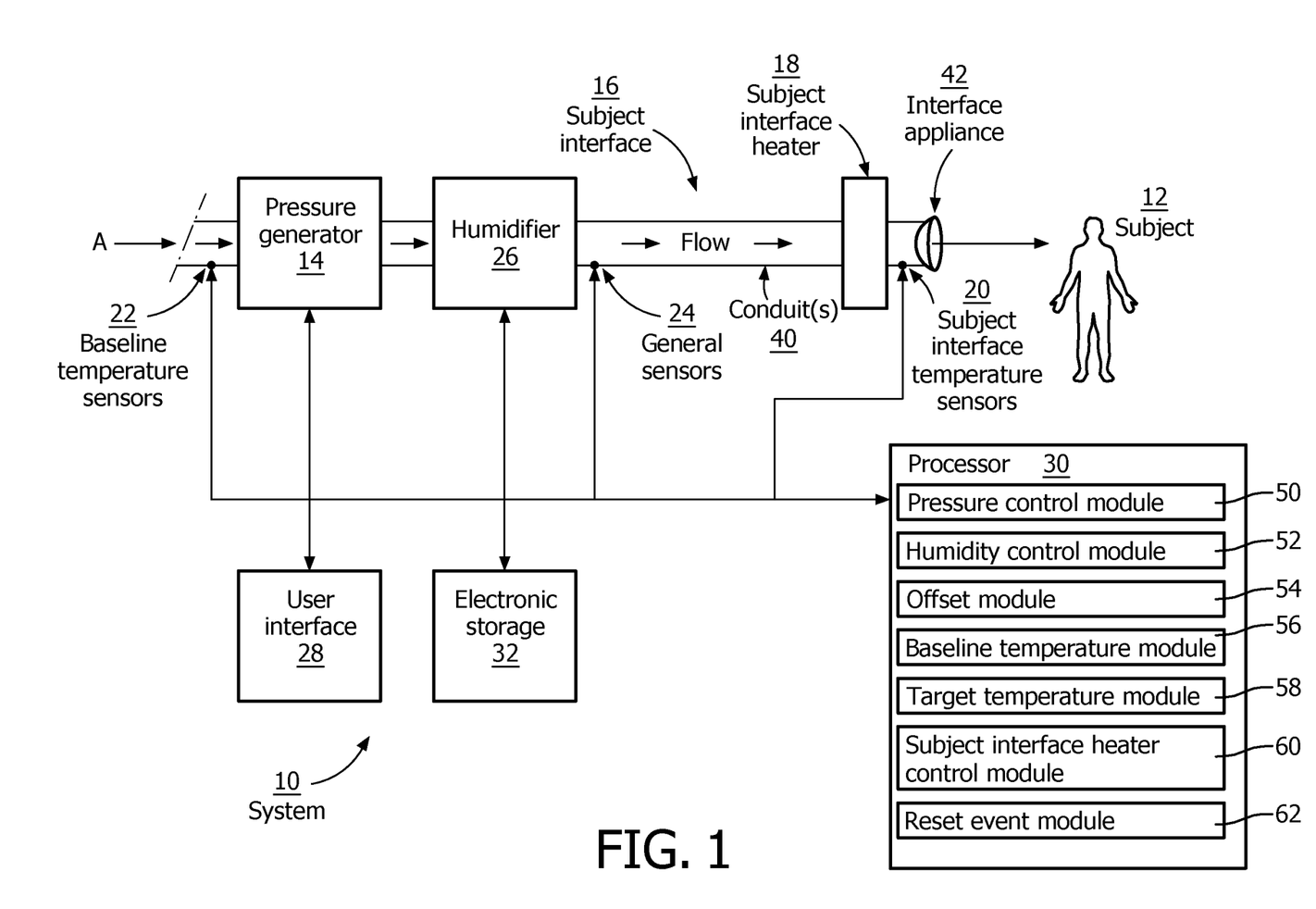
FIG. 1 is a pressure support system configured to provide temperature controlled pressure support to a subject.

FIG. 1 schematically illustrates a pressure support system 10 configured to provide pressure support therapy to a subject 12. Pressure support system 10 is configured to provide the pressure support therapy in the form of a flow of gas that is delivered to the airway of the subject. The pressure support therapy may be dynamic in that one or more parameters of the flow of gas generated by pressure support system 10 may be adjusted based on detection of one or more parameters. For example, pressure of the flow of gas may be increased based on changes to one or more parameters that indicate a respiratory event (e.g., an apnea, snoring, etc.).

Pressure support system 10 is configured to controllably heat the pressurized flow of breathable gas to a target temperature that is offset from a baseline temperature. The breathable gas baseline temperature target offset ensures the gas delivered to subject 12 is delivered at a comfortable temperature and/or humidity level that does not cause airway dryness in subject 12 or result in condensed water in the subject interface. In one embodiment, pressure support system 10 comprises one or more of a pressure generator 14, a subject interface 16, a subject interface heater 18, one or more subject interface temperature sensors 20, one or more baseline temperature sensors 22, one or more general sensors 24, a humidifier 26, a user interface 28, a processor 30, electronic storage 32, and/or other components.

In some embodiments, pressure generator 14 is configured to generate a flow of gas for delivery to the airway of the subject. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control the flow rate and/or pressure of the flow of gas to provide pressure support to the airway of the subject.

Pressure generator 14 receives a flow of gas from a gas source, such as the ambient atmosphere, as indicated by arrow A and elevates the pressure of that gas for delivery to the airway of a patient. Pressure generator 14 is any device, such as, for example, a pump, blower, piston, or bellows, that is capable of elevating the pressure of the received gas for delivery to a patient. The present disclosure also contemplates that gas other than ambient atmospheric air may be introduced into system 10 for delivery to the patient. In such embodiments, a pressurized canister or tank of gas containing air, oxygen, and/or another gas may supply the intake of pressure generator 14. In some embodiments, pressure generator 14 need not be provided, but instead the gas may be pressurized by the pressure of the canister and/or tank of pressurized gas itself.

In one embodiment, pressure generator 14 is a blower that is driven at a substantially constant speed during the course of the pressure support treatment to provide the gas in system 10 with a substantially constant elevated pressure and/or flow rate. Pressure generator 14 may comprise a valve for controlling the pressure/flow of gas. The present disclosure also contemplates controlling the operating speed of the blower, either alone or in combination with such a valve, to control the pressure/flow of gas provided to the patent. An example of a pressure support system suitable for use in the present disclosure is described in U.S. Pat. No. 6,105,575, hereby incorporated by reference in its entirety.

Subject interface 16 is configured to deliver the pressurized flow of breathable gas to the airway of subject 12. As such, subject interface 16 comprises conduit 40, interface appliance 42, and/or other components. Conduit 40 is configured to convey the pressurized flow of gas to interface appliance 42. Interface appliance 42 is configured to deliver the flow of gas to the airway of subject 12. In some embodiments, interface appliance 42 is non-invasive. As such, interface appliance 42 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 42. Some examples of non-invasive interface appliance 42 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance.

Although subject interface 16 is illustrated in FIG. 1 as a single-limbed interface for the delivery of the flow of gas to the airway of the subject, this is not intended to be limiting. The scope of this disclosure comprises double-limbed circuits having a first limb configured to both provide the flow of gas to the airway of the subject, and a second limb configured to selectively exhaust gas (e.g., to exhaust exhaled gases).

Subject interface heater 18 is configured to controllably heat the pressurized flow of breathable gas in subject interface 16. Subject interface heater 18 is illustrated in FIG. 1 at a single location within (or in communication with) conduit 40, near interface appliance 42, and/or within interface appliance 42. The illustrated position of subject interface heater 18 is not intended to be limiting. Subject interface heater 18 may be located in any position that allows it to controllably heat the pressurized flow of breathable gas in subject interface 16. Subject interface heater 18 may be configured to heat the pressurized flow of breathable gas continuously along the entire length of conduit 40. Subject interface heater 18 may be configured to heat the pressurized flow of breathable gas by dissipating electrical current (e.g., resistive heating). Subject interface heater 18 may comprise one or more of a heating coil, a heating jacket, heating tape, and/or other heating devices. Subject interface heater 18 may be configured to heat the gas in subject interface 16 directly and/or indirectly. In some embodiments, a heating coil may be positioned within conduit 40 in fluid communication with the pressurized flow of breathable gas to directly heat the gas flow. In some embodiments, a heating jacket may be placed around conduit 40 to heat the flow of gas indirectly by transferring heat through the wall of conduit 40.

Subject interface temperature sensor(s) 20 are configured to generate one or more output signals conveying information related to the temperature of the pressurized flow of breathable gas in subject interface 16. Although sensor(s) 20 are illustrated in FIG. 1 at a single location in system 10, this is not intended to be limiting. Sensors 20 may comprise multiple sensors disposed in a plurality of locations within subject interface 16, such as for example, at various locations within (or in communication with) conduit(s) 40, within (or in communication with) interface appliance 42, and/or other locations. Output signals generated by subject interface temperature sensors 20 may be transmitted wirelessly and/or via wires.

Baseline temperature sensor(s) 22 are configured to generate one or more output signals conveying information related to a baseline temperature. The baseline temperature may be ambient temperature, a temperature of the gas source from which the pressurized flow of breathable gas is drawn, and/or some other temperature that may fluctuate over time. Although sensor(s) 22 are illustrated in FIG. 1 at a single location in system 10, this location and/or number is not intended to be limiting. Sensors 22 may comprise multiple sensors disposed in a plurality of locations within system 10 and/or in the environment around system 10, such as for example, at various locations within pressure generator 14, within humidifier 26, at a room thermostat that controls the temperature of the room in which subject 12 is sleeping, and/or other locations. In one embodiment, output signals conveying information related to a baseline temperature of the pressurized flow of breathable gas may be generated by subject interface temperature sensors 20 at the beginning of the sleep period of subject 12, before subject interface 16 has been heated by subject interface heater 18. Output signals generated by baseline temperature sensors 22 may be transmitted wirelessly and/or via wires.

One or more general sensors 24 are configured to generate output signals conveying information related to one or more gas parameters of the gas within system 10. The one or more gas parameters comprise flow, volume, pressure, temperature, humidity, velocity, and/or other gas parameters. General sensors 24 may comprise one or more sensors that measure such parameters directly (e.g., through fluid communication with the flow of gas in subject interface 16). General sensors 24 may comprise one or more sensors that generate output signals related to one or more parameters of the flow of gas indirectly. For example, one or more of general sensors 24 may generate an output based on an operating parameter of pressure generator 14 (e.g., a valve driver or motor current, voltage, rotational velocity, and/or other operating parameters), and/or other sensors. Although general sensors 24 are illustrated at a single location within (or in communication with) conduit 40 between humidifier 26 and subject interface heater 18, this is not intended to be limiting. General sensors 24 may comprise sensors disposed in a plurality of locations, such as for example, within pressure generator 14, within (or in communication with) interface appliance 42, and/or other locations. Output signals generated by general sensors 24 may be transmitted wirelessly and/or via wires.

Humidifier 26 is configured to humidify the flow of gas in system 10. In some embodiments, humidifier 26 may comprise a humidification chamber, a gas inlet, a gas outlet, a heating element, and/or other components. In one embodiment humidifier 26 is a warm mist humidifier (e.g., a vaporizer) configured to generate water vapor by heating fluid held within the humidification chamber via the heating element. Humidifier 26 is configured such that the flow of gas is received from pressure generator 14 by humidifier 26 through the gas inlet and is humidified within the humidification chamber by the water vapor before being released from the humidification chamber through the gas outlet. In one embodiment, the gas outlet is connected with subject interface 16 such that the humidified flow of gas is delivered to the airway of subject 12 through subject interface 16. U.S. Patent Application Publication No. 2007/0169776, incorporated herein by reference in its entirety, discloses an exemplary humidifier device suitable for use in the present disclosure. Humidifier devices having alternative designs may also be used.

User interface 28 is configured to provide an interface between system 10 and subject 12 and/or other users through which subject 12 and/or other users may provide information to and receive information from system 10. Other users may comprise a caregiver, a doctor, and/or other users. This enables data, cues, results, and/or instructions and any other communicable items, collectively referred to as "information," to be communicated between a user (e.g., subject 12) and one or more of pressure generator 14, processor 30, and/or other components of system 10. Examples of interface devices suitable for inclusion in user interface 28 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 28 comprises a plurality of separate interfaces. In one embodiment, user interface 28 comprises at least one interface that is provided integrally with pressure generator 14.

It is to be understood that other communication techniques, either hard-wired or wireless, are also contemplated by the present disclosure as user interface 28. For example, the present disclosure contemplates that user interface 28 may be integrated with a removable storage interface provided by electronic storage 32. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 28 comprise, but are not limited to, an RS-232 port, RF link, an IR link, modem (telephone, cable or other). In short, any technique for communicating information with system 10 is contemplated by the present disclosure as user interface 28.

Processor 30 is configured to provide information processing capabilities in system 10. As such, processor 30 may comprise one or more of a digital processor, an analog processor, a digital circuit designed to process information, an analog circuit designed to process information, a state machine, and/or other mechanisms for electronically processing information. Although processor 30 is shown in FIG. 1 as a single entity, this is for illustrative purposes only. In some implementations, processor 30 may comprise a plurality of processing units. These processing units may be physically located within the same device (e.g., humidifier 26), or processor 30 may represent processing functionality of a plurality of devices operating in coordination.

As shown in FIG. 1, processor 30 is configured to execute one or more computer program modules. The one or more computer program modules may comprise one or more of a pressure control module 50, a humidity control module 52, an offset module 54, a baseline temperature module 56, a target temperature module 58, a subject interface heater control module 60, a reset event module 62, and/or other modules. Processor 30 may be configured to execute modules 50, 52, 54, 56, 58, 60, and/or 62 by software; hardware; firmware; some combination of software, hardware, and/or firmware; and/or other mechanisms for configuring processing capabilities on processor 30.

It should be appreciated that although modules 50, 52, 54, 56, 58, 60, and 62 are illustrated in FIG. 1 as being co-located within a single processing unit, in implementations in which processor 30 comprises multiple processing units, one or more of modules 50, 52, 54, 56, 58, 60, and/or 62 may be located remotely from the other modules. The description of the functionality provided by the different modules 50, 52, 54, 56, 58, 60, and/or 62 described below is for illustrative purposes, and is not intended to be limiting, as any of modules 50, 52, 54, 56, 58, 60, and/or 62 may provide more or less functionality than is described. For example, one or more of modules 50, 52, 54, 56, 58, 60, and/or 62 may be eliminated, and some or all of its functionality may be provided by other modules 50, 52, 54, 56, 58, 60, and/or 62. As another example, processor 30 may be configured to execute one or more additional modules that may perform some or all of the functionality attributed below to one of modules 50, 52, 54, 56, 58, 60, and/or 62.

Pressure control module 50 is configured to control pressure generator 14 to generate the flow of gas in accordance with the therapy regime. By way of non-limiting example, processor 30 may control pressure generator 14 such that the pressure support provided to the subject via the flow of gas comprises non-invasive ventilation, positive airway pressure support, continuous positive airway pressure support, bi-level support, BiPAP®, and/or other types of pressure support therapy.

Humidity control module 52 is configured to control the humidity of the pressurized flow of breathable gas. For example, humidity control module 52 may control the heating element in the humidifier to heat and/or vaporize fluid within humidifier 26 to adjust the amount of moisture added to the flow of gas within humidifier 26. The level of humidity to which the flow of gas is adjusted may be dictated by a therapy regime and/or selected by a user (e.g., the subject, a caregiver, a therapy decision-maker, etc.).

Offset module 54 is configured to obtain a temperature offset. The temperature offset may be obtained responsive to information entered by a user via user interface 28 (e.g., a user-selectable setting, and/or other information), obtained from information stored in electronic storage 32, and/or obtained by another method. By way of a non-limiting example, the temperature offset may comprise a numerical temperature offset selected by subject 12 via user interface 28. By way of a second non-limiting example, the temperature offset may comprise the temperature offset from the previous sleep period stored in electronic storage 32.

The temperature offset is the temperature difference from the baseline temperature at which the pressurized flow of breathable gas should be delivered to subject 12. The temperature offset may be selectable from one or more temperature offset options by the user via user interface 28. The one or more selectable temperature offsets may be indicated to the user via user interface 28 by way of numbers, letters, levels (e.g., low, medium, high), and/or other indications. By way of a non-limiting example, subject 12 may select from offset temperature choices of 4, 7, 10, 13, or 16° F. above the baseline temperature. As another example, subject 12 may select from choices of a low, medium, or high offset temperature.

Offset module 54 may be configured to determine the temperature offset from a temperature offset range generated based on past selections of the user, such that the temperature offset may be fine tuned, and/or the range of temperature offsets is most comfortable to the user. The temperature offset, and/or the temperature offset range may be automatically adjusted based on changing ambient conditions, therapy compliance, user input, and/or other factors. Temperature offset module 54 may be configured to tailor the temperature offset and/or temperature offset range to a user based on user input therapy settings for different initial ambient conditions, user input changes during therapy as ambient conditions change, changes in therapy settings and/or ambient conditions correlated to changes in user compliance, responses to a comfort questionnaire posed via user interface 28, and/or other tailoring information.

Baseline temperature module 56 is configured to determine the baseline temperature based on the output signals generated by the baseline temperature sensors. In some embodiments, baseline temperature module 56 may determine the baseline temperature directly from the baseline temperature sensors, determine the baseline temperature based on a calculation, determine the baseline temperature based on data stored in electronic storage 32, and/or determine the baseline temperature based on other factors. For example, the baseline temperature may be determined based on a calculated index wherein the algorithm used to calculate the index comprises input related to multiple baseline temperature sensors (e.g., an average) and/or data stored in electronic storage 32 indicating the average nightly temperature for multiple previous nights.

Target temperature module 58 is configured to determine a target temperature for the flow of breathable gas. The target temperature is determined based on the baseline temperature and/or the temperature offset. In some embodiments, target temperature module 58 is configured to add the temperature offset amount to the baseline temperature to determine the target temperature. In some embodiments and/or at certain times, the target temperature may be fixed even as the baseline temperature varies over a therapy session. For example, target temperature module 58 may determine a target temperature of 75° F. based on a baseline temperature of 70° F. and a temperature offset of 5° F. In this example, the 75° F. target temperature may be fixed even if the temperature of the surrounding environment decreases and/or increases. In some embodiments and/or at certain times, the target temperature may be determined in a dynamic, ongoing manner (e.g., determined at some sampling rate) based on a current determination of the baseline temperature by baseline temperature module 56.

Subject interface heater control module 60 is configured to control subject interface heater 18 to maintain the temperature of the pressurized flow of breathable gas at the target temperature. In some embodiments, subject interface heater control module 60 is configured to control subject interface heater 18 based on output signals from subject interface temperature sensors 20 and/or information from target temperature module 58.

Reset event module 62 is configured to detect a reset event. A reset event may comprise one or more of expiration of a monitored period of time, an arousal event, a baseline temperature change of some amount, wakeful sleep by subject 12, an indication of dryness in the airway of subject 12, a temperature sensor fault condition, a heater fault condition, a change in air flow, a change in interface appliance 42 leakage (e.g., mask leakage), a change in the volume of liquid in humidifier 26 by some amount, changes in humidity control performance, one or more user setting changes, loss of power to pressure generator 14, loss of power to system 10, user response to a comfort questionnaire posed via user interface 28, and/or other reset events. A reset event may comprise an instantaneous occurrence (e.g. expiration of a monitored period of time), and/or conditions/circumstances that last for a period of time. In some embodiments, reset event module 62 may detect a reset event when subject 12 wakes from sleep during a sleep period (instantaneous event). In some embodiments, reset event module 62 may detect a reset event when subject 12 experiences wakeful sleep (e.g. movement, shallow breathing, etc.) over time (lasting condition).

In some embodiments in which the target temperature is held fixed as the baseline temperature varies over a usage session, target temperature module 58 is configured to re-determine the previously fixed target temperature responsive to detection of a reset event. This may include a single re-determination and subsequent fixing of the newly determined target temperature. Re-determination may include, responsive to detection of a reset event by reset event module 62, the target temperature being determined in a dynamic, ongoing manner for a reset time period following detection of a reset event. Responsive to the reset time period ending, the target temperature is fixed by target temperature module 58. In some embodiments, the target temperature may be fixed at the last determined target temperature during the reset time period. In some embodiments, the target temperature may be fixed at a calculated value (e.g., mean, median, etc.) determined from one or more target temperatures determined during the reset time period. For example, subject 12 may wake up during a sleep period causing reset event module 62 to detect a reset event. Responsive to the reset event detection, target temperature module 58 may determine a new target temperature for subject interface heater control module 60. Target temperature module 58 may continue to dynamically determine new target temperatures for the following 30, for example, minutes (reset time period). At the end of the 30 minute reset time period target temperature module 58 may determine a final target temperature and fix the target temperature at the last determined value.

The reset time period may be determined at manufacture, determined by programming the reset time period into processor 30, determined responsive to information entered by a user via user interface 28, determined directly based the one or more output signals generated by one or more sensors 24, determined dynamically based on previous respiration by the subject, and/or determined by another method. For example, the reset time period may comprise a reset time entered by a user via user interface 28. In some embodiments, the reset time period may be determined based on one or more parameters (e.g. breathing parameters of subject 12, gas parameters of system 10, etc.) returning to a steady state and/or equilibrium value. For example, the reset time period may be determined based on output signals from sensors 24 indicating subject 12 has returned to sleep.

In some embodiments, electronic storage 32 comprises electronic storage media that electronically stores information. The electronic storage media of electronic storage 32 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 32 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 32 may store software algorithms, information determined by processor 30, information received via user interface 28, and/or other information that enables system 10 to function properly. Electronic storage 32 may be (in whole or in part) a separate component within system 10, or electronic storage 32 may be provided (in whole or in part) integrally with one or more other components of system 10 (e.g., user interface 28, processor 30, etc.).

Figure 2:
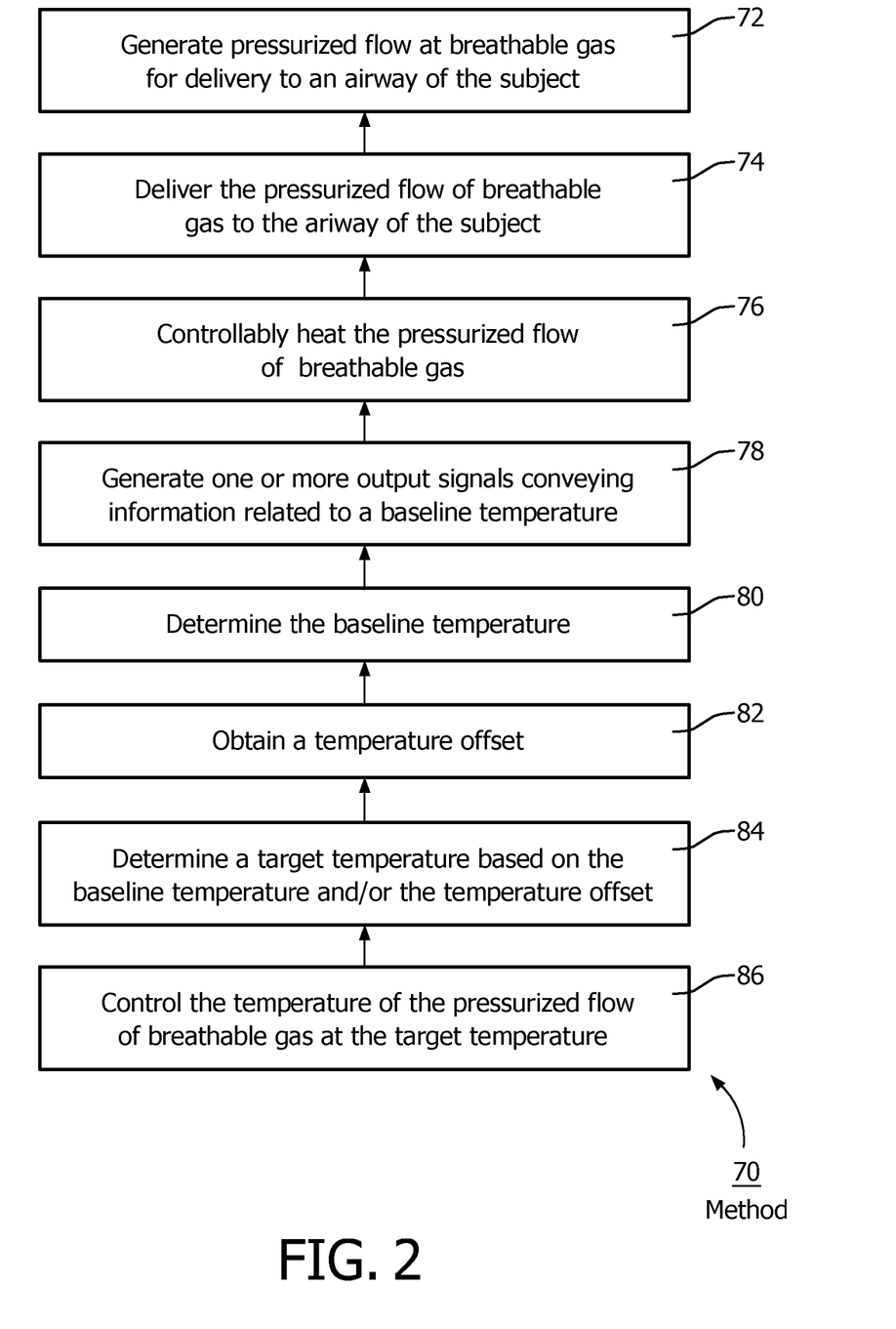
FIG. 2 is a method for providing temperature controlled pressure support to a subject.

FIG. 2 illustrates a method 70 of delivering a humidity controlled pressurized flow of breathable gas to the airway of a subject. The operations of method 70 presented below are intended to be illustrative. In some embodiments, method 70 may be accomplished with one or more additional operations not described, and/or without one or more of the operations discussed. Additionally, the order in which the operations of method 70 are illustrated in FIG. 2 and described below is not intended to be limiting.

In some embodiments, method 70 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 70 in response to instructions stored electronically on an electronic storage medium. The one or more processing devices may include one or more devices configured through hardware, firmware, and/or software to be specifically designed for execution of one or more of the operations of method 70.

At an operation 72, a pressure generator generates a pressurized flow of breathable gas. In some embodiments, operation 72 is performed by a pressure generator the same as or similar to pressure generator 14 (shown in FIG. 1 and described herein).

At an operation 74, the pressurized flow of breathable gas is delivered to an airway of the subject. In some embodiments, operation 74 is performed by a subject interface the same as or similar to subject interface 16 (shown in FIG. 1 and described herein).

At an operation 76, the pressurized flow of breathable gas is controllably heated. In some embodiments, operation 76 is performed by a heater the same as or similar to subject interface heater 18 (shown in FIG. 1 and described herein.)

At an operation 78, one or more output signals conveying information related to a baseline temperature are generated. In some embodiments, operation 68 is performed by a sensor the same as or similar to baseline temperature sensors 22 (shown in FIG. 1 and described herein.)

At an operation 80, the baseline temperature is determined. In some embodiments, operation 80 is performed by a processor module the same as baseline temperature module 56 (shown in FIG. 1 and described herein.)

At an operation 82, a temperature offset is obtained. In some embodiments, operation 82 is performed by a processor module the same as or similar to offset module 54 (shown in FIG. 1 and described herein.)

At an operation 84, the target temperature is determined based on the baseline temperature and/or the temperature offset. In some embodiments, operation 84 is performed by a processor module the same as or similar to target temperature module 58 (shown in FIG. 1 and described herein.)

At an operation 86, the temperature of the pressurized flow of breathable gas is controlled at the target temperature. In some embodiments, operation 86 is performed by a processor module the same as or similar to subject interface heater control module 60 (shown in FIG. 1 and described herein.)

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A pressure support system configured to provide temperature controlled pressure support to a subject, the pressure support system comprising:

a pressure generator configured to generate a pressurized flow of breathable gas for delivery to an airway of the subject;

a subject interface configured to deliver the pressurized flow of breathable gas to the airway of the subject;

a subject interface heater configured to controllably heat the pressurized flow of breathable gas in the subject interface;

one or more baseline temperature sensors configured to generate one or more output signals conveying information related to a baseline temperature; and one or more processors configured to execute computer program modules, the computer program modules comprising:

a baseline temperature module configured to determine the baseline temperature based on the one or more output signals generated by the one or more baseline temperature sensors;

an offset temperature module configured to receive user selection of a temperature offset, the user selection made from a plurality of temperature offset options presented to a user by the offset temperature module via a user interface, the plurality of temperature offset options determined by the offset temperature module based on past temperature offset selections by the user, the plurality of temperature offset options being adjusted by the offset temperature module based on one or more of therapy compliance, user input therapy settings for different initial ambient conditions, user input changes during therapy as ambient conditions change, changes in the ambient conditions correlated to changes in user compliance, or responses to a comfort questionnaire posed via the user interface;

a reset event module configured to detect reset events, the reset events comprising expirations of monitored periods of time;

a target temperature module configured to, responsive to a detection of an individual reset event, determine a target temperature based on the baseline temperature and the temperature offset; and a subject interface heater control module configured to control the subject interface heater to maintain a temperature of the pressurized flow of breathable gas at the target temperature.

2. The system of claim 1, wherein the baseline temperature comprises an ambient temperature.

3. The system of claim 1, wherein the different initial ambient conditions and the ambient conditions comprise one or more of a temperature, pressure, or humidity of an environment around the pressure support system.

4. The system of claim 1, wherein the reset event module is further configured to monitor the monitored periods of time, the temperature controlled pressure support configured to be received by the subject during the monitored periods of time.

5. The system of claim 4, wherein the target temperature module is configured such that, responsive to the detection of the individual reset event by the reset event module, for a predetermined reset time period following the detection of the individual reset event the target temperature is re-determined a plurality of times successively, during the predetermined reset time period, and such that, responsive to the predetermined reset time period ending, the target temperature is fixed at a last determined target temperature determined during the predetermined reset time period.

6. The system of claim 4, wherein the target temperature module is configured such that, responsive to the detection of the individual reset event by the reset event module, for a predetermined reset time period following the detection of the individual reset event the target temperature is re-determined a plurality of times successively during the predetermined reset time period, and such that, responsive to the predetermined reset time period ending, the target temperature is fixed at a calculated value determined from the one or more target temperatures determined during the predetermined reset time period.

7. A method of controlling a temperature of a pressurized flow of breathable gas, the method comprising;
generating the pressurized flow of breathable gas for delivery to an airway of a subject;
delivering the pressurized flow of breathable gas to the airway of the subject;
controllably heating the pressurized flow of breathable gas;
generating one or more output signals conveying information related to a baseline temperature;
determining the baseline temperature based on the one or more output signals conveying the information related to the baseline temperature;
receiving user selection of a temperature offset, the user selection made from a plurality of temperature offset options presented to a user via a user interface, the plurality of temperature offset options determined based on past temperature offset selections by the user; the plurality of temperature offset options being adjusted based on one or more of therapy compliance, user input therapy settings for different initial ambient conditions, user input changes during therapy as ambient conditions change, changes in the ambient conditions correlated to changes in user compliance, or responses to a comfort questionnaire posed via the user interface;
detecting reset events, wherein the reset events comprise expirations of monitored periods of time;
determining, responsive to detection of an individual reset event, a target temperature based on the baseline temperature and the temperature offset; and
controlling the temperature of the pressurized flow of breathable gas at the target temperature.

8. The method of claim 7, wherein the baseline temperature comprises an ambient temperature.

9. The method of claim 7, wherein the different initial ambient conditions and the ambient conditions comprise one or more of a temperature, pressure, or humidity of an environment around the subject.

10. The method of claim 7, further comprising:
monitoring the monitored periods of time; the subject receiving the pressurized flow of breathable gas during the monitored periods of time.

11. The method of claim 10, wherein responsive to the detection of the individual reset event, for a predetermined reset time period following the detection of the individual reset event, the target temperature is re-determined a plurality of times successively during the predetermined reset time period, and such that, responsive to the predetermined reset time period ending, the target temperature is fixed at a last determined target temperature determined during the predetermined reset time period.

12. The method of claim 10, wherein responsive to the detection of the individual reset event, for a predetermined reset time period following the detection of the individual reset event, the target temperature is re-determined a plurality of times successively during the predetermined reset time period, and such that, responsive to the predetermined reset time period ending, the target temperature is fixed at a calculated value determined from the one or more target temperatures determined during the predetermined reset time period.

13. A pressure support system configured to provide temperature controlled pressure support to a subject; the pressure support system comprising:
means to generate a pressurized flow of breathable gas for delivery to an airway of the subject;
means to deliver the pressurized flow of breathable gas to the airway of the subject, wherein the means to deliver the pressurized flow of breathable gas to the airway of the subject comprises a means to communicate with the airway of the subject;
means to controllably heat the pressurized flow of breathable gas in the means to communicate with the airway of the subject;
means to generate one or more output signals conveying information related to a baseline temperature; and
means to execute computer program modules, the computer program modules comprising:
means to determine the baseline temperature based on the one or more output signals generated by the means to generate the one or more output signals conveying information related to the baseline temperature;
means to receive user selection of a temperature offset, the user selection made from a plurality of temperature offset options presented to a user by the means to receive via a user interface; the plurality of temperature offset options determined by the means to receive based on past temperature offset selections by the user, the plurality of temperature offset options being adjusted by the means to receive based on one or more of therapy compliance, user input therapy settings for different initial ambient conditions, user input changes during therapy as ambient conditions change, changes in the ambient conditions correlated to changes in user compliance, or responses to a comfort questionnaire posed via the user interface;
means to detect reset events, wherein the reset events comprise expirations of monitored periods of time;
means to determine, responsive to detection of an individual reset event, a target temperature based on the baseline temperature and the temperature offset; and
means to control the means to controllably heat the pressurized flow of breathable gas to maintain a temperature of the pressurized flow of breathable gas at the target temperature.

14. The system of claim 13, wherein the baseline temperature comprises an ambient temperature.

15. The system of claim 13, wherein the different initial ambient conditions and the ambient conditions comprise one or more of a temperature, pressure, or humidity of an environment around the pressure support system.

16. The system of claim 13, wherein the means to detect the reset events is further configured to monitor the monitored periods of time, the temperature controlled pressure support is configured to be received by the subject during the monitored periods of time.

17. The system of claim 16, wherein the means to determine the target temperature is configured such that, responsive to the detection of the individual reset event by the means to detect the reset events, for a predetermined reset time period following the detection of the individual reset event, the target temperature is re-determined a plurality of times successively during the predetermined reset time period, and such that, responsive to the predetermined reset time period ending, the target temperature is fixed at a last determined target temperature determined during the predetermined reset time period.

18. The system of claim 16, wherein the means to determine the target temperature is configured such that, responsive to the detection of the individual reset event by the means to detect the reset event, for a predetermined reset time period following the detection of the individual reset event, the target temperature is re-determined a plurality of times successively during the predetermined reset time period, and such that, responsive to the predetermined reset time period ending, the target temperature is fixed at a calculated value determined from the one or more target temperatures determined during the predetermined reset time period.

\* \* \* \* \*